(12) United States Patent
Janin et al.

(10) Patent No.: US 6,316,636 B1
(45) Date of Patent: *Nov. 13, 2001

(54) SYNTHESIS OF FLUOROCARBON COMPOUNDS

(75) Inventors: Robert Janin, Corbas; Laurent Saint-Jalmes, Meyzieu, both of (FR)

(73) Assignee: Rhone-Poulenc Chimie, Courbevoie Cedex (FR)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/608,519

(22) Filed: Feb. 28, 1996

(30) Foreign Application Priority Data

Feb. 28, 1996 (FR) ................................................ 95 02290

(51) Int. Cl.$^7$ ..................... C07D 231/16; C07D 319/08; C07C 21/18; C07C 19/08
(52) U.S. Cl. .................................. 548/375.1; 548/377.1; 549/484; 560/153; 562/125; 568/56; 568/65; 568/677; 568/683; 568/684; 568/681
(58) Field of Search ............................. 549/484; 568/56, 568/65, 677, 683, 684, 681, 375.1, 377.1; 562/125; 560/153

(56) References Cited

U.S. PATENT DOCUMENTS 5,196,599  3/1993  Filligan et al. .................... 568/590

FOREIGN PATENT DOCUMENTS 0423009  4/1991  (EP) .................................... 549/290
0590459  4/1994  (EP) .................................... 549/290

OTHER PUBLICATIONS

Journal of Fluorine Chem., vol. 59, No. 3, 12/92 Lausanne, Ch., pp. 417–422, Mori Meto Et Al.
Tetrahedron Letters, vol. 22, No. 21, 1981 Oxfords, ,GB, pp. 1997–2000, Suda et al (Copy to Follow).
Journal of Organic Chemistry, vol. 44, No. 4, 2/79, Wash., D.C., pp. 563–569, J. F. Harris, Jr. (Copy to Follow).
J. Chem, Soc. Perkin Trans., vol. 1992, pp. 3371 to 3375.

*Primary Examiner*—Floyd D. Higel
(74) *Attorney, Agent, or Firm*—Burns, Doane, Swecker & Mathis, L.L.P.

(57) ABSTRACT

Fluorocarbon compounds are synthesized by reacting a substrate hydrocarbyl compound containing at least one $sp^3$-hybridized halophoric carbon atom bearing at least two halogen atom substituents, at least one of which is a halogen atom having an atomic number greater than that of fluorine and the at least one halophoric carbon atom being bonded to at least one chalcogen, with at least one reactant which comprises a complex of a Bronstedt base with a defined amount n of hydrofluoric acid, n being at least 3 and not greater than 20.

43 Claims, No Drawings

SYNTHESIS OF FLUOROCARBON COMPOUNDS

BACKGROUND OF THE INVENTION

1. Technical Field of the Invention

The present invention relates to the synthesis of hydrocarbon compounds which are fluorinated on a carbon atom of an "alkyl" moiety thereof via exchange between a halogen atom having an atomic number greater than fluorine, employing a fluorine-containing reactant which is at least partially in the form of a complex salt.

This invention more especially relates to a process for the preparation of fluorocompounds that are fluorinated on a carbon atom bearing substituent groups which are electron-withdrawing (or attracting) by means of an inductive effect.

2. Description of the Prior Art

Fluorocompounds are characteristically difficult to prepare. The reactivity of fluorine is such that it is difficult, or even impossible, to directly prepare fluoro derivatives.

One of the most commonly used techniques for preparing fluoro derivatives entails reacting a halogen compound, generally a chloro derivative, and exchanging the halogen with an inorganic fluorocompound, generally an alkali metal fluoride, typically of high atomic weight.

In general, the fluoride employed is potassium fluoride, which provides a satisfactory economic compromise.

Under these conditions, many processes such as, for example, those described in French Certificate of Addition No. 2,353,516 and in the article *Chem. Ind.*, 56 (1978), have been carried out industrially to produce aryl fluorides, onto the aryl moieties of which electron-withdrawing groups are grafted.

Except in the instances where the substrate is particularly suitable for this type of synthesis, this technique presents drawbacks, the principal ones of which are those analyzed below.

The subject reaction requires reactants such as alkali metal fluorides, for example potassium fluoride, which are relatively expensive vis-a-vis the technical specifications they must satisfy in order to be suitable for this type of synthesis; they must be very pure, dry and in a suitable physical state.

In addition, this reaction is not operative for an entire class of compounds, in particular those bearing substituents on the halophoric carbon atom (namely, on the carbon atom bearing the halogen or halogens destined to be exchanged with fluorine).

Reactants such as hydrofluoric acid in liquid form, or diluted with dipolar aprotic solvents, are also used. However, hydrofluoric acid is too powerful or harsh a reactant and often results in unwanted polymerization reactions or in tars.

In this event, and especially in the case where it is desired to obtain derivatives fluorinated on a carbon atom of an alkyl radical (including aralkyl) rendered electron-deficient by the presence of electron-withdrawing groups, this art is faced with an alternative which is not encouraging; either very harsh conditions are selected, and tars are especially obtained, or mild reaction conditions are adopted and, in the best of scenarios, the substrate is unchanged. Lastly, the literature describes exchanges carried out utilizing hydrofluoric acid salt reactants in the presence of heavy elements in oxide or fluoride form. Among the elements thus used, antimony and heavy metals such as silver and quicksilver (mercury) are exemplary.

Another disadvantage is the selectivity of the reaction: when there are more than one halogen to be exchanged on the same carbon atom, it is often difficult to exchange less than all of same.

SUMMARY OF THE INVENTION

Accordingly, a major object of the present invention in the provision of an improved exchange reaction between, on the one hand, heavy halogen atoms such as chlorine and, on the other, fluorine, while is significantly enhancing the specificity of the reaction.

Another object of the present invention is the provision of an improved exchange reaction between the heavy halogens such as chlorine and fluorine, carried out under particularly mild reaction conditions. Yet another object of this invention is the provision of an improved such process which permits utilizing a source of fluoride whose morphology is less critical.

Still another object of this invention is the provision of an improved such process which permits exchange of only one out of two or three possible halogen atoms.

And yet another object of the present invention is the provision of an improved such process which permits exchange of only two out of three possible halogen atoms.

Another object of this invention is the provision of an improved such process which permits exchange of molecules or atoms to obtain carbon atoms which bear only one fluorine atom simultaneously with one or two other halogen atoms different from fluorine.

Yet another object of the present invention is the provision of an improved such process which permits exchange of molecules or atoms to obtain carbon atoms which bear only two fluorine atoms simultaneously with one other halogen atom which is different from fluorine.

Yet another object of this invention is the provision of an improved such process which avoids the use of a large amount of metals considered to be expensive or toxic, such as mercury and/or silver.

Still another object of this invention is the provision of an improved such process which permits reducing the amounts of metals considered to be expensive or toxic, such as mercury and/or silver, such that the molar ratio between the metal and the substrate whose halogen atoms are to be exchanged is at a value at most equal to 0.5, advantageously at most 0.2, preferably at most 0.1.

And another object of the present invention is the provision of an improved such process which permits avoiding entirely the use of metals considered to be expensive or toxic, such as mercury and/or silver, such as not to add to the reaction mixture any of the elements indicated above; in other words, such that the concentrations of each of said metals do not exceed values of $10^{-3}$ M, advantageously $10^{-4}$ M, preferably $10^{-5}$ M.

Briefly, the present invention features a process for the synthesis of fluorocarbon compounds, comprising reacting a substrate containing at least one $sp^3$-hybridized halophoric carbon atom bearing at least two halogen atom substituents, at least one of which is a halogen atom having an atomic number greater than that of fluorine, said at least one halophoric carbon atom being bonded to at least one chalcogen, with at least one reactant which comprises the combination of a Bronstedt base with a defined amount n of hydrofluoric acid, n being at least equal to 3 and at most equal to 20, preferably at most 10.

DETAILED DESCRIPTION OF BEST MODE AND PREFERRED EMBODIMENTS OF THE INVENTION

More particularly according to the present invention, it has now been determined that certain carbon atoms bearing groups which are electron-withdrawing by an inductive effect are capable of reacting with a reactant of the above type, on condition that at least one of the electron-withdrawing groups is a chalcogen.

The reaction temperature ranges from the melting point of the reaction mixture to its decomposition or boiling point, generally from 0° C. to 150° C., advantageously from 20° to 100° C.

The subject process is advantageously carried out at atmospheric pressure, but it can be conducted at pressures of up to 20 $10^5$ pascals.

Exemplary preferred bases include those which are trivalent hydrocarbon derivatives of elements of column VB, advantageously from a period ranking at least equal to the second and generally less than the sixth, of the Periodic Table of the Elements (supplement to the *Bulletin de la Société Chimique de France*, No. 1, January 1966). Other than those described below, exemplary such compounds are trivalent derivatives, which, when they are trisubstituted, are in fact pnictines, these pnictines being more fully described below.

Among said hydrocarbon derivatives of the elements of column V, preferred are those which are derived from hydrogen pnictides by total or partial substitution of the hydrogen with hydrocarbon residues, which may be bonded to the atom from column VB via a double bond (as in the imines), or a triple bond (as in the nitrites).

However, the hydrocarbon derivatives of the elements of column V are advantageously derived from hydrogen pnictides by total or partial substitution of the hydrogen by monovalent hydrocarbon residues, advantageously with alkyl radicals [in the present description, "alkyl" is used in its etymological sense to be the hydrocarbon residue of an alcohol after removing the alcohol (or -ol) function]; these alkyl compounds will, by analogy with the term pnictide, be denoted in the present description by the term "pnictines."

Thus, in the case of nitrogen, the substitution of hydrogen nitride (ammonia) provides amines, in the case of phosphorus, the substitution of hydrogen phosphide provides phosphines, in the case of arsenic, the substitution of hydrogen arsenide provides arsines and in the case of antimony, the substitution of hydrogen antimonide (or stibide) provides stibines. They are advantageously selected from among the hydrocarbon derivatives of phosphorus, such as the phosphines.

Moreover, the weaker and softer the base, the better and more complete is the exchange. Thus, primary, secondary and preferably tertiary amines provide reactants which contain few HF groups (not more than 5, generally fewer) and which are less powerful than the bases of aromatic heterocyclic type in which the hetero atom, or at least one of the hetero atoms, is selected from column V.

These compounds formed of a base and a distinct number of HF molecules will be designated below by the term "HF-base" or "base-HF" complex(es).

The present invention does not feature exchanges with metal fluorides (in particular alkali metal fluorides such as KF, CsF, etc.), which may be expressed by the fact that the amount [(expressed in equivalents) of (alkali metal, ammonium) cation(s)] must be at least equal to once (advantageously at least to ⅓ times, preferably to approximately twice) that of hydrogen in the form of free proton, released halohydric acid or "base-HF" complexes including "F-(HF)."

The following empirical rule is presented: if the bases form definite compounds of more than 5 HF per basic function, this is then a powerful reactant capable of exchanging two heavy halogens on the same carbon atom under very mild conditions, and even three under slightly harsher conditions (temperature and pressure). Otherwise, it is a more selective reactant which exchanges, in general, only to provide a single fluorine on a carbon atom under mild conditions and two fluorine atoms on the so-called halophoric carbon under more severe conditions. This invention is especially advantageous for replacing chlorine atoms by fluorine atoms.

Thus, the exchange reactions are essentially successive (in effect, each additional fluorine atom on the halophoric carbon slows the exchange of halogen atoms heavier than fluorine with the latter), thereby making it possible to carry out a selective or complete exchange, by varying the operating conditions and the choice of reactants. As it is generally possible to establish conditions under which the exchange reaction ceases before all of the halogen atoms heavier than fluorine have been replaced thereby, it follows that twofold selectivity is possible. On the one hand, it is possible to exchange only a limited number of halogen atoms heavier than fluorine and, on the other, it is also possible to treat an already partially fluorinated mixture and to significantly modify only the molecules which have not attained the desired number of fluorine atoms.

In general, the ease of exchange of a halogen atom heavier than fluorine with the latter increases with its atomic number.

As is apparent, the stoichiometry and the stoichiometric excess may be varied in order to limit the number of halogen atoms exchanged per molecule.

There may exist several halophoric carbon atoms per molecule. It is preferable for two halophoric atoms not to interfere with each other. A typology of carbon atoms, or even of molecules, most likely to exchange their heavy halogens with fluorine under the influence of the above reactants will be given below. Each characteristic set forth below enhances the benefits of the invention for said carbons.

Thus, it is particularly preferred for the possible residual bond of the halophoric carbon atom advantageously to be a bond with a substituent group selected from among groups which are electron-withdrawing by means of an inductive effect. The said group selected from among the electron-withdrawing groups is advantageously a halogen.

In order to attain good reactivity, it is preferable that the sum of the number of atoms of the said chalcogen(s) to be at least equal to 10. In other words, if there is only one chalcogen, it is preferable for it to be a chalcogen heavier than oxygen. It is particularly advantageous when at least one of the chalcogens is a sulfur atom.

It is particularly preferred that said halophoric carbon bears at least two halogen atoms of atomic number higher than that of fluorine.

Thus, as will later be seen, it is particularly advantageous that said halophoric carbon be trihalomethyl, namely, when it bears three halogen atoms advantageously selected from between chlorine and fluorine.

Regarding said chalcogen(s), it should be appreciated that it is preferably divalent (oxidation number=−2) when it is alone, and, when there are two, at least one of them is divalent, the other possibly being simply electron-withdrawing, on account, for example, of donor-acceptor type bonding between the said chalcogen [with the condition, of course, that it is not oxygen, for obvious chemical reasons] and oxygen (for example sulfone or sulfoxide).

Thus, to summarize the above, suitable substrates include molecules having the formula (I):

$$R—CXX'—Y(O)_r—R_5 \quad (I)$$

wherein R is a hydrocarbon residue, a halogen, an electron-withdrawing group or a hydrocarbylchalcogenyl group such as an alkoxyl or aryloxy radical, or the sulfur, selenium or tellurium counterparts thereof: X and X', which may be identical or different, are each a halogen, preferably chlorine (with the proviso that R, X and X' cannot simultaneously be fluorine and that at least one of them is a halogen heavier than fluorine which is to be exchanged with fluorine); Y is a chalcogen, advantageously from an atomic row higher than oxygen, in particular when R is other than hydrocarbylchalcogenyl and with the proviso that, when Y is oxygen, r is equal to zero; r is zero or an integer selected from betweem one and two and is advantageously less than 2; and $R_5$ is any radical, advantageously a hydrocarbon radical.

When the radical R bears no divalent chalcogen (namely, one in which the two doublets are available), it is preferable for r to be less than two, preferably equal to zero.

When $R_5$ is electron-withdrawing, especially via mesomeric effect, it should be appreciated that the exchange is more difficult, especially for the third fluorine atom on the same carbon.

Thus, for complete exchange, it is desirable that said chalcogen be linked via its second bond to an atom which is electron-donating via an inductive or mesomeric effect. Said electron-donating atom may be another chalcogen (which is a donor via a mesomeric effect), advantageously from an atomic row higher than that of oxygen.

The electron-donating atom may also be a carbon atom of an alkyl radical, or of an electron-rich aryl radical. In this event, the alkyl is advantageously an aralkyl radical, preferably a benzyl radical, and the electron-rich aryl radical is advantageously a five-membered heterocyclic radical or six-membered homocyclic radical.

Thus, for an exchange providing three fluorine atoms on the same halophoric carbon atom, it is preferable for $R_5$ to be alkyl, namely, for its attachment bond to be carried by an $sp^3$-hybridized carbon; advantageously, said $sp^3$-hybridized carbon bears substituents which overall constitute a non-withdrawing or weakly withdrawing moiety (i.e., less withdrawing than dichlorophenyl). Preferably, said $sp^3$-hybridized carbon atom bears at least one and advantageously two hydrogen atoms.

The reaction may proceed when R is equal to H, when at least one of the following two conditions is satisfied:
(i) the reactant is a powerful reactant (i.e., if the bases form specific compounds containing more than 5 HF per basic function);
(ii) it is preferable for the sum of the atomic numbers of the chalcogen(s) to be at least equal to 10.

However, in general, even so, this value R=H is not preferred.

$R_5$ advantageously is, in particular:
(a) optionally substituted aryl, in particular heteroaryl;
(b) alkyl and in particular:

—CR'R"—Ar;

wherein R' and R", which may be identical or different, are each hydrogen, or an aryl or lower alkyl radical (namely, having from 1 to 4 carbon atoms) and, preferably, one or both are advantageously hydrogen; and Ar is a radical having at least one double bond and in which the carbon atom from which the double bond depends is an $sp^1$ carbon and preferably an $sp^2$ carbon. Ar is advantageously a lower aryl, preferably having not more than 10 carbon atoms and advantageously being homocyclic;

—CR'R"—CR$_1$R$_2$—EWG;

wherein the radicals R' and R" are as defined above; EWG is an Electron-Withdrawing Group, a group which stabilizes a double bond or a leaving group; and $R_1$ and $R_2$, which may be identical or different, are each a hydrogen or halogen atom, or a hydrocarbon radical, in particular an alkyl, alkyne, alkene or aryl radical; one or both are advantageously hydrogen atoms.

Each radical R and $R_5$ typically contains not more than 30 atoms (of which not more than 20 are carbon atoms), advantageously 20 atoms (of which not more than are carbon atoms), and preferably not more than 15 carbon and/or nitrogen atoms (of which not more than 12 are carbon atoms). The total number of carbons in the substrate molecules only rarely is greater than 50, and advantageously is not more than 30.

When $R_5$ is aryl, particularly exemplary are those compounds in which:
R is lower alkyl [optionally substituted, and in particular halogenated (including perhalogenated and in particular perfluorinated)], halogen, aryl or Ar'O— and Ar'S—, in which Ar' is a lower aryl (namely, containing not more than 10 carbon atoms);
$R_5$ is an optionally substituted phenyl radical, an optionally substituted heterocycle, advantageously a five-membered heterocycle, preferably one containing two hetero atoms (it is desirable to have two nitrogen atoms); thus, for example, the radical —Y(O)$_r$—R$_5$ advantageously corresponds to the formula:

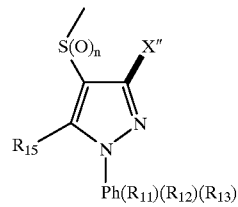

wherein n has the same values as r, namely 0, 1 or 2; $R_{11}$ and $R_{12}$, which may be identical or different, advantageously in the ortho position, are each hydrogen or a halogen; $R_{13}$, advantageously in the para position, is a halogen, an alkyl group optionally substituted by one or more halogen atoms (including a group selected from among the perfluoroalkyl radicals), an alkyloxyl group optionally substituted by one or more halogens (including a group selected from among perfluoroalkyloxyl radicals), or an $SF_5$ radical; X" is a nitrile function or a halogen atom; and $R_{15}$ is an amino group, optionally mono- or disubstituted with radicals (the same or different, in the case of disubstitution) selected from among alkyl radicals optionally substituted by one or more halogens (including perfluoroalkyl radicals), acyl radicals optionally substituted by one or more halogens (including perfluoroacyl radicals) or alkyloxycarbonyl radicals.

The alkyl, alkyloxyl and acyl radicals are preferably light or lower, i.e., they contain not more than four carbon atoms.

It should be appreciated that when $R_{13}$ is an alkyloxyl group optionally substituted by several halogen atoms and when at least one of said halogen atoms is from an atomic row higher than that of fluorine, there are two possible carbon centers of exchange.

The residues $R_5$ and R may constitute one and the same radical, but this being a divalent radical.

For example, they may together form an aryl radical, the points of attachment being borne either by two carbons on the same ring and in a vicinal position to each other; or by two carbons beta to each other, not belonging to the same ring, but the two rings of which are fused and condensed (e.g., the instance of two alpha positions of naphthalene or equivalents); or by two carbons γ to each other belonging to rings separated by a third ring, in the manner of phenanthrene.

By way of examples of such formulae, the following are presented:

Vicinal carbons on the same ring:

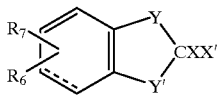

with the proviso that Y' can be either a single bond or a chalcogen (with the same preferences as Y), or a methylene radical optionally mono- or disubstituted with halogens, or a divalent group —Y"—CΞΞ'— or —CΞΞ'—Y"—, with the further proviso that Y" can have the same definition as Y, and Ξ and Ξ' the same values as X and X', respectively (Ξ and Ξ' may simultaneously be fluorine); $R_6$ and $R_7$ are each, independently, hydrogen, a halogen, a nitro group, a nitrile, a hydrocarbon group, advantageously having not more than 5 carbon atoms, an alkyl group optionally substituted by one or more halogen atoms (including a group selected from among the perfluoroalkyl radicals), an alkyloxyl group optionally substituted by one or more halogen atoms (including a group selected from among the perfluoroalkyloxyl radicals), or an $SF_5$ radical.

And, in particular:

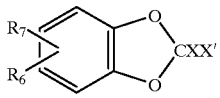

Carbons on two separate rings with $R_8$ having the same values as $R_6$ or $R_7$:

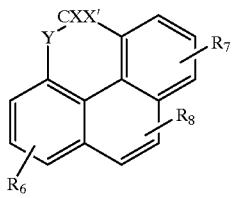

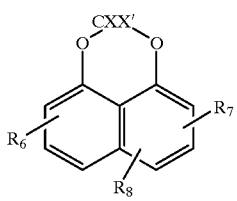

In a preferred embodiment of the invention, cleavages (or lyses) may be carried out in order to form compounds which are particularly useful for organic synthesis and for the synthesis of chalcogenophoric acids (and in which the chalcogen is from a row at least equal to that of sulfur). The oxidation of the compounds according to the invention may be carried out using peroxides and, in particular, those of hydrogen (aqueous hydrogen peroxide solution and various hydroperoxides [for example acyl hydroperoxides and alkyl hydroperoxides]) under conditions which are per se known to this art, or by halogens and in particular chlorine. In this embodiment, it is often advantageous for the chalcogen to be sulfur and for it to include a subsequent step of oxidation of said sulfur atom. The oxidation step is advantageously carried out in order to obtain said sulfur atom in the form of a sulfone. The oxidation may also be carried out in order to obtain said sulfur atom in the form of a sulfoxide, of a sulfenate, or in an equivalent oxidation state.

This embodiment may subsequently include a downstream step of hydrolysis, advantageously in an alkaline medium, to provide a corresponding sulfinic or sulfonic acid salt.

This type of reaction may produce, according to the particular reaction Conditions, either sulfenyls or sulfoxides, or, lastly, as indicated above, may include lyses to produce sulfonic or sulfinic acids, or equivalents thereof when the chalcogen is selenium or tellurium instead of sulfur.

In addition, it has now surprisingly been determined that if only the stoichiometric amount or a slight stoichiometric excess is used (amount of halogen ranging from 0.5 to 1.5 SA, advantageously from 8 to 1.3, preferably from 0.9 to 1.2 SA), sulfenates whose carbon vicinal to the sulfur is perfluorinated produce the sulfinyl halide when they are oxidized with halogen atoms (advantageously chlorine).

The halogenation is carried out by subjecting the sulfenate, advantageously diluted in a very non-polar (i.e., unable to dissolve more than 5% mass of water), essentially anhydrous (i.e., where the content in water represents at most ⅓ in mole of the substrate, advantageously at most ⅕, preferably at most ⅒) and chlorine-insensitive solvent, to the action of chlorine in an at least substantially stoichiometric amount, at a temperature at most equal to 100° C., advantageously ranging from 0° C. to 50° C.

The subject reaction can be represented as follows:

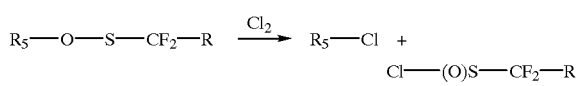

This reaction is of particular interest for the radicals R containing not more than 10 carbon atoms. It proceeds all the better the more stable the carbonation $R_5^+$; thus, for the latter reaction, $R_5$ is advantageously benzylic, allylic or tert-alkyl. Hence, among the appropriate substrates are those of formula II, wherein Y is sulfur or a higher chalcogen and r is equal to 1 and oxygen is advantageously intercalated between Y and CR'R".

It will be appreciated that the halides, and in particular sulfinyl chlorides (of type R—$CF_2$—SO—) are particularly important synthetic intermediates.

Molecules which are particularly suitable for this reaction are especially those of formula (II), derived from the formula I:

wherein R is a halogen, electron-withdrawing group, hydrocarbyl radical such as an alkyl or aryl radical, or a hydrocarbylchalcogenyl radical such as an alkoxyl or aryloxyl radical, and the sulfur, selenium and tellurium counterparts thereof; X is a halogen, preferably chlorine and especially fluorine; Y is a chalcogen, advantageously from an atomic row higher than oxygen and with the proviso that, when Y is oxygen, r is equal to zero; r is zero or an integer selected from between one or two; R' and R", which may be identical or different, are each an aryl or lower alkyl radical, or preferably, one or both are hydrogen atoms; and Ar is a compound having at least one double bond and in which the carbon atom from which the double bond depends is an $sp^1$ carbon and preferably an $sp^2$ carbon. Ar is advantageously a lower aryl radical, preferably having not more than 10 carbon atoms and advantageously being homocyclic.

In another preferred embodiment of the present invention, the compounds of formula:

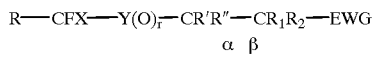

$$R-CFX-Y(O)_r-CR'R''-CR_1R_2-EWG$$
$$\alpha \quad \beta$$

are subjected to a β-elimination. In the formula immediately above, one, advantageously at least two, of the radicals R', R", $R_1$ and $R_2$ is a hydrogen atom (it is desirable for one of the radicals on each of the α and β carbons to be hydrogen); and EWG is an Electron-Withdrawing Group, a group which stabilizes a double bond, or a leaving group (in the event that it is desired to form, by β-elimination with cleavage between the β carbon and the EWG, a derivative of the formula —CFX—Y(O)$_r$—CR'R"=CR$_1$R$_2$).

Electron-withdrawing groups which are exemplary are halogen atoms, groups containing a carbonyl function (such as amides, esters, ketones and aldehydes), groups derived from a carbonyl function (such as imines, amidines, oximes, thioketones, thioesters, thioamides and thioloesters), nitrites, pnictoniums (in particular phosphoniums and ammoniums; see below), the nitro group, ortho esters, radicals in which at least the atom vicinal to the free bond (or open bond, i.e., the bond which links the radical to the remainder of the molecule considered) is perhalogenated and, in particular, perfluorinated; thus, perfluoroalkyl radicals such as trifluoromethyl and pentafluoroethyl are suitable, as are 1,1-difluoro radicals and 1,1,2,2-tetrafluoroalkyl radicals, such as 1,1-difluoroethyl, 1,1-difluoro- and 1,1,2,2-tetrafluoropropyl.

Other electron-withdrawing groups include groups derived from oxygenated chalcogens (such as sulfoxides and sulfones), or from elements of column VB of the Periodic Table such as phosphine oxides and phosphonic or phosphinic acid esters; the free bond is advantageously borne by the metalloid (chalcogen or element from column VB).

Again in the event of β-eliminations, exemplary leaving groups, other than the halogens indicated above, include the pseudohalogens as described below. A "pseudohalogen" is considered to be a radical (in general this radical comprises a light chalcogen (sulfur or preferably oxygen) via which it is bonded to the remainder of the molecule) which, on leaving, forms an anion whose associated acid has an acidity (measured by the Hammett constant) at least equal to that of acetic acid. Among the typical pseudohalogens which are exemplary are the alkyloxyl radicals corresponding to the acids perhalogenated in the alpha-position of the acyloxyl function, such as trifluoroacetoxy (CF$_3$—CO—O—), and especially sulfonyloxyl radicals, especially those in which the carbon bearing the sulfur is perfluorinated, an example of which is trifluoromethanesulfonyloxy (CF$_3$—SO$_2$—O—).

According to the present invention, those pseudohalogens which, on leaving, have an acidity at least equal to that of sulfonic acids, such as tosyl (example of arylsulfonic acids), or mesyl (example of alkylsulfonic acids) are preferred.

Consistent herewith, a pnictonium is a tertiary pnictine quaternized with a hydrocarbyl radical (such as an aryl or alkyl radical, including the aralkyl radicals).

Said pnictines are trivalent hydrocarbon derivatives of the elements of column VB of the Periodic table. They are derived from the hydrogen pnictides by total or partial substitution of the hydrogen with hydrocarbon residues which may be bonded to the atom from column VB via a double bond (as in the imines) or a triple bond (as in the nitriles).

However, the hydrocarbon derivatives of the elements from column V are advantageously derived from hydrogen pnictides by total or partial substitution of the hydrogen by monovalent hydrocarbon residues, advantageously by alkyl radicals ["lalkyl" is again used in its etymological sense, to be an alcohol hydrocarbon residue after removing the alcohol (or -ol) function]; these compounds derived from pnictide are, by analogy with the term pnictide, denoted in the present description by the term pnictines.

Thus, in the case of nitrogen, the substitution of hydrogen nitride (ammonia) provides amines, in the case of phosphorus, the substitution of hydrogen phosphide provides phosphines, in the case of arsenic, the substitution of hydrogen arsenide provides arsines and in the case of antimony, the substitution of hydrogen antimonide (or stibide) provides stibines. They are advantageously selected from among the phosphorus hydrocarbon derivatives such as phosphines.

In general, it is desirable for the β-elimination to be carried out with cleavage between the $Y(O)_r$ and CR'R" moieties, in which event at least one of $R_1$ and $R_2$ must be hydrogen and, also in which event, it is preferable for EWG to represent an electron-withdrawing (or attracting) group or a group which stabilizes a double bond. Exemplary groups which stabilize a double bond include those which comprise a bond capable of being conjugated with a possible double bond between the α and β carbons; other than the electron-withdrawing radicals containing a double bond indicated above, exemplary such groups include the alkynes, alkenes and aryls.

It is also desirable for EWG to be sufficiently electron-withdrawing to stabilize a carbanion in the β-position; when EWG is aryl and, in particular, an optionally substituted phenyl radical, it is desirable for $R_1$ and/or $R_2$ themselves to be selected from among suitable EWG-containing radicals and, in particular, from alkynes, alkenes and aryls.

Lastly, still in the event of a β-elimination with cleavage between the $Y(O)_r$ and CR'R" moieties, it is desirable for EWG to be a mediocre leaving group and advantageously one which is not as good a leaving group as R—CFX—Y(O)$_r$—. It is also advantageous for r to be at least equal to 1, preferably at least equal to 2.

The reaction is carried out under conditions and according to techniques per se known to this art, using strong bases whose pKa of the associated acid is advantageously at least equal to 14.

To determine the conditions for any particular reaction, empirical rules which may be used in the majority of situations are given below.

As aforesaid, "hydrocarbylchalcogenyl" is a radical of the structure $R_6$—Y"—, wherein $R_6$— is a hydrocarbon radical, i.e., a radical containing at least hydrogen and carbon and in which the atom from which the bond depends (here with Y") is a carbon atom, and wherein Y" is a chalcogen (oxygen, sulfur, selenium or tellurium). $R_6$ is advantageously an alkyl radical [optionally substituted, and in particular halogenated (including perhalogenated and in particular perfluorinated radicals)], or an optionally substituted aryl radical.

The definitions of the radicals are in respect of the formula (I):

$$R—CXX'—Y(O)_r—R_5 \quad (I)$$

By the expressions "electron-donating" and "weakly electron-withdrawing" are intended as withdrawing as or less withdrawing than a dichlorophenyl function (this definition also being suitable for non-electron-withdrawing aryl). Conversely, by "electron-withdrawing" or "significantly electron-withdrawing," which here have the same meaning, as may be deduced from the above definition, are intended the opposite of "electron-donating and weakly electron-withdrawing," i.e., more withdrawing than a dichlorophenyl function.

One example (more precisely, one paradigm) of the weak reactants (see the above empirical rule) is the compound defined as triethylamine·3 HF.

One example (more precisely, one paradigm) of the strong reactants (see the above empirical rule) is the compound defined as pyridine·10 HF.

Mild conditions: θ=melting point at not more than 50° C.;

Harsh conditions: 50° C. to 100° C. (or at the boiling point, if this is lower at the pressure considered);

Very harsh conditions: θ=100° to 150° C. and, where appropriate, pressures above atmospheric pressure;

In the event that, in the formula (I), X and X' represent halogens heavier than fluorine, the reaction equations may be expressed as follows:

Reaction Providing a Fluorine Atom on the Halophoric Carbon:

Reactions Leading Providing Two Fluorines on the Halodhoric Carbon:

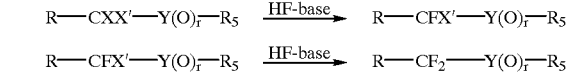

and with R representing a halogen heavier than fluorine:

Reactions Providing Three Fluorine Atoms on the Halophoric Carbon:

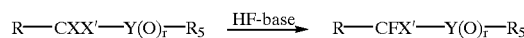
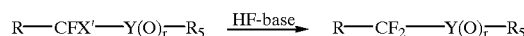
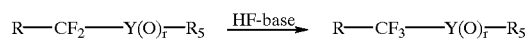

Compare also the following summary Table I:

TABLE I

| | | | | After exchange (i.e., after reaction with the various reagents), final number of fluorine atoms on the haloporic atom according to the following reactants used | | | |
|---|---|---|---|---|---|---|---|
| Structure of the substrate molecule | | | | Weak reactant | Strong reactant | Strong reactant | Strong reactant |
| Value of R | Value of $R_5$ | Value of $r$ | Weak reactant mild conditions | harsh conditions | mild conditions | harsh conditions | very harsh conditions |
| Electron-withdrawing aryl | Electron-donating or weakly electron-withdrawing | 0 | 0–1 | 1 | 1 | 1–2 | 2 |
| Electron-withdrawing aryl | Significantly electron-withdrawing | 0 | 0–1 | 1 | 1 | 1–2 | 2 |
| Electron-withdrawing aryl | Any | 1 | 0–1 | 0–1 | 0–1 | 1–2 | 1–2 |
| Non-electron-withdrawing aryl | Electron-donating or weakly electron-withdrawing | 0 | 1 | 1–2 | 1–2 | 2 | 2 |
| Non-electron-withdrawing aryl | Significantly electron-withdrawing | 0 | 1 | 1–2 | 1–2 | 2 | 2 |
| Non-electron-withdrawing aryl | Any | 1 | 0–1 | 0–1 | 1–2 | 1–2 | 2 |
| Alkyl | Electron-donating or weakly electron-withdrawing | 0 | 1–2 | 2 | 2 | 2 | 2 |
| Alkyl | Significantly electron-withdrawing | 0 | 1 | 1–2 | 1–2 | 1–2 | 2 |
| Alkyl | Any | 1 | 0–1 | 1–2 | 1–2 | 1–2 | 2 |
| Hydrocarbyl-chalcogenyl | Electron-donating or weakly electron-withdrawing | 0 | 1–2 | 2 | 2 | 2 | 2 |
| Hydrocarbyl-chalcogenyl | Significantly electron-withdrawing | 0 | 1 | 1–2 | 1–2 | 1–2 | 2 |
| Hydrocarbyl-chalcogenyl | Any | 1 | 1 | 1–2 | 1–2 | 1–2 | 2 |
| Halogen heavier than fluorine | Electron-donating or weakly electron-withdrawing | 0 | 1–2 | 2 | 2–3 | 3 | 3 |

TABLE I-continued

| | | | | After exchange (i.e., after reaction with the various reagents), final number of fluorine atoms on the haloporic atom according to the following reactants used | | | |
|---|---|---|---|---|---|---|---|
| Structure of the substrate molecule | | | | Weak reactant | Strong reactant | Strong reactant | Strong reactant |
| Value of R | Value of $R_5$ | Value of $\underline{r}$ | Weak reactant mild conditions | harsh conditions | mild conditions | harsh conditions | very harsh conditions |
| Halogen heavier than fluorine | Significantly electron-withdrawing | 0 | 1 | 1–2 | 1–2 | 2–3 | 2–3 |
| Halogen heavier than fluorine | Any | 1 | 1 | 1–2 | 1–2 | 2–3 | 2–3 |

In order to further illustrate the present invention and the advantages thereof, the following specific examples are given, it being understood that same are intended only as illustrative and in nowise limitative.

EXAMPLE 1

Preparation of HF-base Solutions; General Procedure

The various HF-base media were synthesized as follows:

To x mol of an organic base (pyridine, triethylamine, dioxane, etc.) or inorganic base (KF, $Bu_4NF$, etc.) with stirring (optionally cooled to −20° C.) were added dropwise y mol of anhydrous hydrofluoric acid. After addition of the anhydrous hydrofluoric acid, the reaction medium was heated to room temperature and employed without any treatment. The HF-base complex thus had the structure $(HF)_y$-$base_x$.

After the reaction, when the fluorination crude was treated with an anhydrous organic phase which was immiscible with the HF-base medium considered, but which was capable of dissolving the products formed (for example only $CH_2Cl_2$ (without ice or water)), two phases were obtained: the less polar phase (for example $CH_2Cl_2$) which contained the product obtained after exchange, and the more polar phase "HF-base" which could then be recycled, optionally after adjusting it to the initial titer (of HF) and removal of the halohydric acid released by the reaction (for example by distillation). This recycling was specific to the process according to the present invention and provided an additional advantage thereto.

EXAMPLE 2

Cl-F Exchange Using Benzyl Trichloramethyl Sulfide

Synthesis of the Substrate
Reaction Equation:

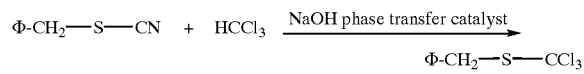

Procedure Employed:

Benzyl trichloromethyl sulfide 1 was obtained according to the technique of M. Makosza (*Synthesis*, 274 (1974)).

(2a) Exchange of Three Chlorine Atoms:
Reaction Equation:

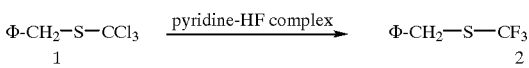

Procedure Employed:

90.1 g (0.374 mol) of the sulfide 1 were added to 297 g of pyridine-$[HF]_{11}$ complex (prepared from 77.3 g of pyridine and 219.7 g of anhydrous hydrofluoric acid) cooled to 0° C.

The reaction medium was then warmed to room temperature and stirred for 18 h.

The crude reaction medium was then poured onto a mixture of $CH_2Cl_2$ (5200 ml) and ice (500 g).

The organic phase was washed 4 times with 100 ml of water and dried over magnesium sulfate. The solvent ($CH_2Cl_2$) was evaporated off to provide 68 g of sulfide 2 (95% relative to 1) which could be purified by distillation (bp=77/30 mm Hg).

$^{19}F$ NMR=35.9 ppm (reference: TFA—trifluoroacetic acid).

When the crude fluorination medium was poured onto $CH_2Cl_2$ alone (without ice or water), two phases were obtained: the $CH_2Cl_2$ phase which contained the sulfide 2, and the pyridine-HF phase which could be recycled.

(2b) Reaction Equation:

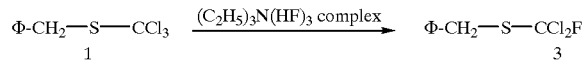

Procedure Employed:

2 g (8.3 $10^{-3}$ mol) of sulfide 1 were added to 20 ml of $Et_3N$—$(HF)_3$ complex at room temperature. The reaction medium was stirred for 4 h at 20° C. and then poured into a mixture of $CH_2Cl_2$ (100 ml) and 25 g of ice and 50 ml of water. The organic phase was washed 3 times with water (50 ml) and then dried over $MgSO_4$. Evaporation of the solvent provided 1.7 g of the sulfide 3 (91.5%).

(2c) Reaction Equation:

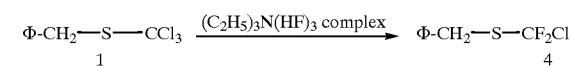

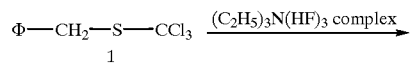

15
-continued

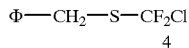

Procedure Employed:

The conditions were the same as in the above reaction, but the reaction medium was stirred for 18 h at 75° C. The treatment was the same as in the above test, and provided 1.64 g of sulfide 4 (95% relative to 1).

$^{19}$F NMR=50.8 ppm (reference TFA).

EXAMPLE 3

Exchanae on 2-Chlorocyclohexyl Trichloromethyl Sulfide

Reaction Equation:

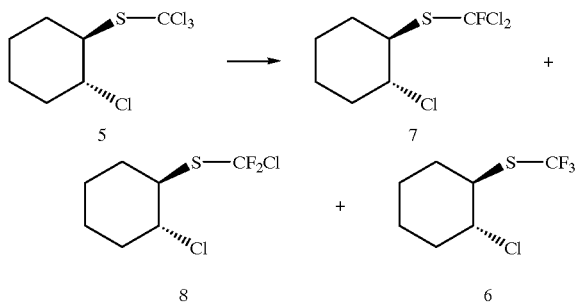

Procedure Employed:

The initial sulfide (labelled 5) (2-chlorocyclohexyl trichloromethyl sulphide) was obtained by trans-addition of CCl$_3$SCl to cyclohexene.

1 g (3.73 10$^3$ mol) of the sulfide 5 was added to the pyridine-[HF]$_{10}$ complex (5 g) cooled to 0° C. The reaction medium was then stirred for 6 h at room temperature before being poured onto a mixture of CH$_2$Cl$_2$ (50 ml) and ice-water (50 g).

The organic phase was washed 3 times with 50 ml of water and then dried over MgSO$_4$. The solvent was evaporated off to provide 0.73 g of sulfide 6 (90% relative to 5).

$^{19}$F NMR=167 ppm (reference TFA[trifluoroacetic acid]).

(3b) Partial Exchange:

1 g (3.73 10$^{-3}$ mol) of sulfide 5 was added at room temperature to 10 ml of the Et$_3$N- [HF]$_3$ complex. The reaction medium was stirred for 5 h at room temperature. The treatment was the same as in the above test, and provided 0.85 g of sulfide 7 (91% relative to 5) accompanied by the sulfide 8.

EXAMPLE 4

Synthesis of Triflinic Acid (trifluormethanesulfinic acid)

Reaction Equations:

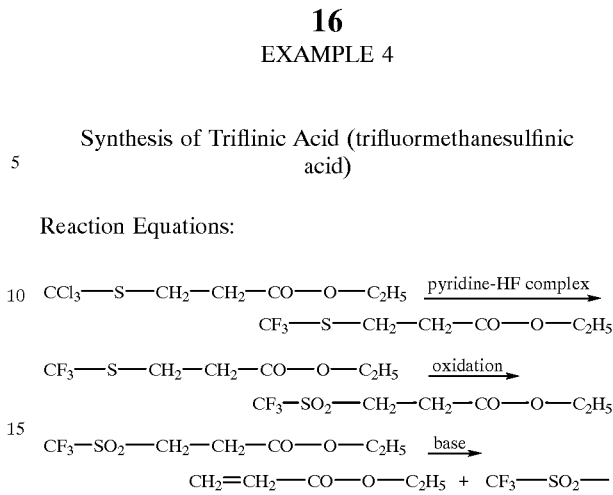

(4a) Exchance on CCl$_3$S(CH$_2$)$_2$CO$_2$Et (9):

Procedure Employed:

100 mg of sulfide 9 were added at 0° C. to 1 ml of pyridine- [HF]$_{10}$ complex. The reaction medium was then stirred for 24 h at room temperature and then poured onto a mixture of CH$_2$Cl$_2$ (20 ml) and ice-water (20 g).

The CH$_2$Cl$_2$ phase was washed 3 times with 10 ml of water, dried over MgSO$_4$ and the CH$_2$Cl$_2$ solvent was then evaporated off to provide a yellow oil (80 mg) which contained about 50% of sulfide 10.

$^{19}$F NMR of the sulfide 10: −41.93 ppm (% CFCl$_3$).

EXAMPLE 5

Exchanae on Pyrazole Derivatives

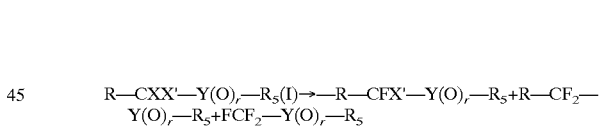

wherein R=halogen (in this instance chlorine); X=X'= chlorine; Y=S; r=0 and R$_5$=

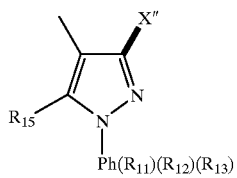

wherein X"=nitrile; R$_{11}$=R$_{12}$ =ortho-chloro and R$_{13}$=para-trifluoromethyl.

General Procedure:

The trichloromethyl pyrazole 11 was added to an HF$_x$-base$_y$ mixture (x and y are known). The reaction mixture was stirred at a given temperature and for a given period of time.

After returning to room temperature, the crude reaction medium was poured onto a CH₂Cl₂/ice-water mixture. The CH₂Cl₂ organic phase was washed 3 times with water and dried over MgSO₄, then the solvent was evaporated off.

The crude products obtained were analyzed by HPLC.

The results of the principal tests thus performed are reported in the Table II which follows:

TABLE II $$R_5\text{-SCCl}_3 \rightarrow R_5\text{SCF}_n\text{Cl}_{3-n}$$
$$n = 1 \text{ to } 3$$

| Nature of the complex | No. of equivalents of base-HF complex relative to R-CXX'-SR₅ | T° | Duration | Yield of exchange product where X = X' = R = F | Yield of exchange product where X = X' = F R = C | Yield of exchange product where X = F X' = R = Cl |
|---|---|---|---|---|---|---|
| Pyridine-[HF]₁₀ | 13 eq | 100° C. | 4 h | 7.2% | 61% | 17.5% |
| Pyridine-[HF]₁₀ | 26 eq | 100° C. | 5 h | 2.3% | 88% | 7.0% |
| Pyridine-[HF]₅ | 24 eq | 100° C. | 10 h | 0.5% | 54.6% | 8.5% |
| Pyridine-[HF]₅ | 48 eq | 100° C. | 24 h | 1.3% | 80.4% | 1.3% |
| Pyridine-[HF]₁₆ | 9 eq | 100° C. | 4 h | 18% | 37% | — |
| Et₃N-[HF]₃ | 30 eq | 80° C. | 6 h | — | 3.5% | 85% |

EXAMPLE 6

Cl-F Exchange on Dichloro-MDB

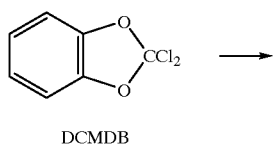

DCMDB (6a) Exchange with Pridine-[HF]₁₀:

Measurement of the yield was semi-quantitative (GC analysis).

191 mg (1 mmol) of DCMDB were added at 0° C. to 2 ml of pyridine-[HF]₁₀. The reaction medium was stirred for 2 h at room temperature and then poured onto a CH₂Cl₂/ice-water mixture. After washing the organic phase, GC analysis provided.

DFMDB=95% (GC area)
DCMDB=difficult to quantify (at most equal to 1%)
chlorofluoro-MDB=1%
(6b) Exchange with Et₃N-[HF]₃:

Measurement of the yield was semi-quantitative (GC analysis).

191 mg of DCMDB were added to 2 ml of Et₃N-[HF]₃ at 0° C.

The reaction time at room temperature was 3 h.
The treatment was the same as in the above test.
The GC analysis indicated:

DFMDB=90% GC area
DCMDB=difficult to quantify (at most equal to 10%)
(6c) DCMDB→DFMDB exchanae with "catalytic" HF+base media:

In the following tests, the amount of base (organic or inorganic) was much smaller than in the above tests. The catalytic base-HF complexes were formed in the same manner as the base-HF complexes used above.

The Table III below reports the influence of a catalytic amount of base (Et₃N and KF) relative to a "blank" test without added base.

Treatment of the tests with catalytic base-HF was the same as those for the tests with pyridine-[HF]₁₀ and Et₃N-[HF]₃.

TABLE III

| HF | DCMB | Base | HF/DCMDB ratio | Base (DCMDB) ratio | DFMDB assayed (GC) | Assayed | Insoluble product |
|---|---|---|---|---|---|---|---|
| 48 g 2.4 mol (4.8 eq) | 95.6 g 0.5 mol | | 4.8 | | 75.5% | 2.4% | 2.9 g |
| 48 g 2.4 mol (4.8 eq) | 95.6 g 0.5 mol | Et₃N 4.72 10⁻² mol | 4.8 | 0.095 eq | 81% | 1.1% | 1.2 g |
| 48 g 2.4 mol (4.8 eq) | 95.6 g 0.5 mol | KF 4.2 10⁻² mol | 4.8 | 0.084 eq | 80.4% | 1.7% | 0.4 g |

EXAMPLE 7

Oxidation to Provide a Sulfenate

Reaction Equation:

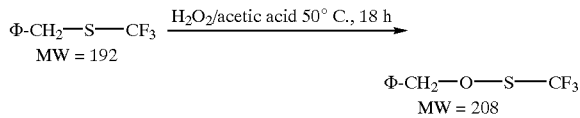

Procedure Employed:

To 192 mg (1 eq) of benzyl trifluoromethyl sulfide diluted in 1 ml of acetic acid was added 0.11 ml (1.1 eq) of 30% aqueous hydrogen peroxide solution.

The medium was heated at 50° C. for 18 h. The crude reaction medium was taken up in dichloromethane and the organic phase was washed with water and then dried over sodium sulfate. After evaporation, a white solid was obtained which was identified as the expected sulfenate, in an amount corresponding to a yield of 90%.

EXAMPLE 8

Oxidation of the Sulphenate

Reaction Equation:

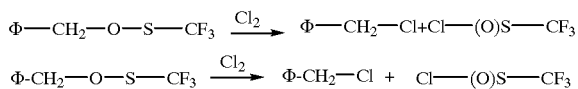

Procedure Employed:

To 208 mg (1 eq) of trifluormethyl benzyl sulfenate diluted in 2 ml of methylene chloride (namely, dichloromethane, $CH_2Cl_2$) were added 71 mg (1.1 eq) of gaseous chlorine. After 18 h at room temperature, gas chromatographic analysis (often denoted by its initials: GC) evidenced that the conversion of the substrate was complete and also yields of benzyl chloride and of trifluoromethane-sulphinyl chloride Of 75% and 80% respectively.

EXAMPLE 9

Synthesis of $PhCH_2SCCl_3$

Benzyl thiocyanate (29.8 g, 0.2 mol), chloroform (76 g, 0.6 mol) and triethylbenzylammonium chloride (0.5 g, 0.002 mol) were stirred vigorously. 40 ml of 50% aqueous sodium hydroxide were added clowly to this solution (mildly exothermic). The temperature increased to 40° C. and was maintained threat for 4 h with efficient stirring.

The reaction mass was then diluted with water and extracted with chloroform. The combined organic phases were washed with water, dried over $MgSO_4$ and concentrated on a rotary evaporator under reduced pressure.

EXAMPLE 10

Synthesis of $PhCH_2SO_2CF_3$

From $PhCH_2SCF_3$:

12.7 ml of 30% aqueous hydrogen peroxide solution (124.3 mmol) were introduced dropwise onto henzyl trifluoromathyl sulfide (5.96 mg, 31.06 mmol) in solution in 23 ml of 99% acetic acid. After stirring for 2 h at 90° C., the reaction mass was diluted with water and extracted with ether (3×100 ml). The organic phase was washed with 3×75 ml of water, 2×75 ml of saturated $NaHCO_3$ solution and 2×75 ml of water. It was then dried over $MgSO_4$ and concentrated on a rotary evaporator under reduced pressure. The solid obtained was recrystallized from $CCl_4$ (25 to 30 ml). 4.604 g of white solids were obtained, the structure and purity of which were monitored NMR. Yield of isolated product=66%.

$^1H$ NMR ($CDCl_3$):

4.47 ppm (s, 2H);

7.43 ppm (m, 5H, aromatic H).

$^{19}F$ NMR ($CDCl_3$):

−76.91 ppm (s).

EXAMPLE 11

Synthesis of 1,2-Diphenylethyl Triflone

Benzyl triflone (0.673 g, 3 mmol) was dissolved in 12 ml of dry acetonitrile. $K_2CO_3$ (0.485 g, 3.5 mmol) was then introduced, followed by benzyl bromide (0.365 ml, 3 mmol). The reaction mass was maintained at reflux (82° C.) for 20 h. It was then filtered, diluted with water and extracted with ether (2×25 ml). The combined organic phases were washed with water (2×20 ml) and with saturated NaCl solution (1×20 ml).

After drying over $MgSO_4$ and concentrating on a rotary evaporator under pressure, a yellow oil was obtained. The product was recrystallized from 3 ml of petroleum ether. Yield of isolated product=68% to 82% (0.637 g to 0.768 g of white solid) characterized by NMR.

$^1H$ NMR ($CDC_{l3}$): 3.39 ppm (dd. 1H, $^2J=13.6$ Hz, $^3J=3.2$ Hz, $H_2$ or $H_3$); 3.77 ppm (dd. 1H, 2J=13.6 Hz, $^3J=11.6$ Hz, $H_3$ or $H_2$); 4.54 ppm (dd. 1H, $^3J=3.2$ Hz, $^3J=11.6$ Hz, $H_1$); 6.92 to 7.35 ppm (m, 10H, aromatic H); $^{19}F$ NMR ($CDCl_3$): −73.80 ppm (s).

EXAMPLE 12

Synthesis of the Triflinate by β-Elimination on 1,2-Diphenylethyl Triflone

Base: DBU (diazabicycloundecene):

The triflone (186 mg, 0.592 mmol), DBU (104 mg, 0.655 mmol) and 1,4-dioxane (3.2 ml) were heated at 100° C. for 67 h. After cooling, the reaction mass was diluted with 20 ml of dichloromethane and washed with 10 ml of water. The aqueous phase was extracted with 2×20 ml of dichloromethane. The aqueous phase was isolated.

The combined organic phases were washed with 1×15 ml of water (which was added to the above aqueous phase), 2×20 ml of water and 1×20 ml of saturated NaCl solution. After drying over $MgSO_4$ and concentrating on a rotary evaporator under reduced pressure, 134 mg of a yellowish-white solid were recovered, which product was analyzed by $^1H$ NMR ($CDCl_3$). This was a mixture containing:

(1) trans-stilbene (spectrum identical with the reference found in the literature (20))

(2) starting material (spectrum identical with that described above)

(3) unidentified impurities

The proportion of trans-stilbene relative to the starting material was 70/30 (mol %).

The isolated aqueous phase was basified by addition of 5.9 ml of 0.1 N sodium hydroxide solution. It was then extracted with 4×30 ml of dichloromethane (extraction of the DBU), neutralized with 0.1 N hydrochloric acid, extracted with 4×20 ml of toluene (extraction of the organic residues) and concentrated on a rotary evaporator under reduced pressure. The oily yellow deposit obtained (116 mg) was characterized and assayed by NMR (standard: $CF_3CH_2OH$). Yield=2%.

$^{19}F$ NMR ($H_2O$): −87.2 ppm (s, $CF_2SO_2Na$).

Base: NaH:

Sodium hydride as a 50% suspension in oil (29 mg, 0.604 mmol) was introduced into a 10 ml round-bottomed flask. The flask was flushed with nitrogen. 3 ml of THF were introduced, followed by 1,2-diphenylethyl triflone (188 mg, 0.599 mmol) in solution in 1 ml of THF. The medium was stirred at room temperature under a stream of nitrogen. After stirring for 6 h, more sodium hydride was added (10 mg, 0.208 mmol). The reaction was monitored by GC (the retention times of the starting material and the possible products formed were known by virtue of authentic samples).

Base: NaOMe:

760 mg of 1,2-diphenylethyl triflone (2.42 mmol), 408 mg of sodium methoxide (7.55 mmol) and 10 ml of anhydrous methanol were stirred at 60° C. for 24 h.

The reaction mass was then concentrated on a rotary evaporator under reduced pressure and diluted in 45 ml of an ether/water mixture (2/1), and the phases were separated out after settling had taken place. The aqueous phase was extracted with 4×25 ml of $CH_2Cl_2$. The combined organic phases were washed with 1×25 ml of water, and this was added to the beginning aqueous phase, 2×40 ml of water and 1×40 ml of brine.

After drying over $MgSO_4$ and concentrating on a rotary evaporator under reduced pressure, 0.747 g of a yellowish-white solid was recovered, which product was analyzed by $^1H$ NMR ($CDCl_3$). This was a mixture containing:

(1) 1.82 mmol trans-stilbene (75% yield)(spectrum identical with the reference described in the literature)
(2) 0.58 starting material (24% yield)(spectrum identical with that described above)

The shifts δ were the same as above.

The aqueous phase was treated with a 6N HCl solution until a pH of about 6 was attained, and concentrated in a rotary evaporator under reduced pressure. Recovered was 0.541 g of white solids analyzed by $^{19}F$ NMR (standard: $CF_3CH_2OH$). Yield=72% in sodium triflinate by spectra identical to that as described above.

The aqueous phase isolated was acidified by addition of HCl 6N solution until pH 5 was attained and concentrated on a rotary evaporator under reduced pressure. The white solid was characterized and assayed by NMR (standard: $CF_3CH_2OH$). Yield in triflinate=72%.

EXAMPLE 13

Synthesis of the Potassium Triflinate by β-Elimination on Ethyl 3-phenyl-3-(trifluoromethanesulfonyl)propionate Benzyl triflone (559 mg, 2.5 mmol), potassium carbonate (1043 mg, 7.55 mmol) and 10 ml of acetonitrile were charged into a 25 ml round-bottomed flask. Ethyl bromoacetate (300 yl, 2.65 mmol) was introduced therein in a single portion. The flask was then closed and heated at 80° C. with stirring for 16 h.

After cooling, the reaction mass was diluted in 30 ml of water and 60 ml of $Et_2O$. The mixture was separated by settling of the phases. The aqueous phase was extracted with 40 ml of $Et_2O$. The combined organic phases were washed with 4×40 ml of water. After drying over $MgSO_4$ and concentrating on a rotary evaporator under reduced pressure, 400 mg of yellow liquid were obtained. Yield=88% of product, characterized by $^1H$ NMR.

All of the aqueous phases were combined, neutralized with 0.1 N HCl solution and concentrated on a rotary evaporator under reduced pressure (τ=65° C.), The residual water was removed by azeotropic entrainment with toluene. 1.156 g of white solid was thus obtained, which product was analyzed by $^{19}F$ NMR (standard: $CF_3CH_2OH$). Yield=68%. The potassium triflinate was extracted with 8×10 ml of ethyl acetate. 390 mg of white solid were isolated. Yield=49% of isolated product, characterized by $^{19}F$ NMR.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A process for the synthesis of a fluorocarbon compound, comprising reacting:
   a hydrocarbyl compound containing an $sp^3$-hybridized halophoric carbon atom bearing at least two halogen atom substituents, at least one halogen atom having an atomic number greater than that of fluorine and said halophoric carbon atom being bonded to a sulfur atom; with
   a Bronstedt base wherein said Bronstedt base is a trivalent hydrocarbon derivative of elements of column VB of the Periodic Table complexed with a defined amount n of hydrofluoric acid, n being at least 3 and not greater than 20.

2. The process as defined by claim 1, wherein said halophoric carbon atom is bonded to an electron-withdrawing group.

3. The process as defined by claim 2, wherein said electron-withdrawing group is a halogen atom.

4. The process as defined by claim 1, said halophoric carbon atom bearing at least two halogen atoms having atomic numbers greater than that of fluorine.

5. The process as defined by claim 1, said halophoric carbon atom bearing three halogen atoms selected from the group consisting of chlorine and fluorine, said halogen atoms being the same or different, except that if the halogens are the same, they are not fluorine.

6. The process as defined by claim 1, said sulfur atom being divalent.

7. The process as defined by claim 1, said sulfur atom being bonded to an electron-donating moiety.

8. The process as defined by claim 7, wherein said electron-donating moiety is a chalcogen other than oxygen.

9. The process as defined by claim 1, wherein said electron-donating moiety is an alkyl.

10. The process as defined by claim 1, wherein said sulfur atom is part of a sulfone moiety.

11. The process as defined by claim 10, wherein said sulfur atom is in the form of a sulfinic or sulfonic acid salt.

12. The process as defined by claim 10, wherein said sulfur atom is in the form of a sulfoxide or sulphenate.

13. The process as defined by claim 1, wherein said Bronstedt base is selected from the group consisting of a pnictine and an aromatic heterocycle.

14. The process as defined by claim 1, comprising introducing at least one fluorine atom onto said halophoric carbon atom.

15. The process as defined by claim 14, comprising introducing at least two fluorine atoms onto said halophoric carbon atom.

16. The process as defined by claim 14, comprising introducing at least three fluorine atoms onto said halophoric carbon atom.

17. A process for the synthesis of a mixed halogen fluorocarbon compound comprising reacting:
   a hydrocarbon compound containing an $sp^3$-hybridized halophoric carbon atom bearing at least two halogen atom substituents, wherein at least two of the halogens have an atomic number greater than that of fluorine and said halophoric carbon atom is bonded to at least one chalcogen; with
   a Bronstedt base, wherein said Bronstedt base is a trivalent hydrocarbon compound of an element of column VB of the periodic table complexed with n molecules of hydrofluoric acid where n is at least 3 and not greater than 20; and
   wherein said mixed halogen fluorocarbon compound has at least one more fluorine atom on the halophoric carbon atom than did the hydrocarbon compound and has retained at least one halogen having an atomic number greater than that of fluorine on the halophoric carbon atom.

18. The process of claim 17, wherein said halophoric carbon atom is bonded to an electron-withdrawing group.

19. The process of claim wherein said chalcogen has an atomic number of at least 10.

20. The process of claim 17, wherein said halogen having an atomic number greater than that of fluorine is chlorine.

21. The process of claim 17, wherein said chalcogen is divalent.

22. The process of claim 17, wherein said chalcogen is bonded to an electron-donating group.

23. The process of claim 22, wherein said electron-donating group is a chalcogen other than oxygen.

24. The process of claim 22, wherein said electron-donating group is an alkyl.

25. The process of claim 17, wherein said chalcogen is sulfur.

26. The process of claim 25, wherein said sulfur is part of a sulfone moiety.

27. The process of claim 25, wherein said sulfur is part of a sulfinic or sulfonic acid salt.

28. The process of claim 25, wherein said sulfur is part of a sulfoxide or a sulphenate.

29. The process of claim 17 wherein said Bronstedt base is $(CH_3CH_2)_3N \cdot 3HF$.

30. A process for the synthesis of a fluorocarbon compound comprising reacting:
   a hydrocarbon compound containing an $sp^3$-hybridized halophoric carbon atom bearing at least two halogen atom substituents, wherein at least one of the halogens have an atomic number greater than that of fluorine and said halophoric carbon atom is bonded to a sulfur atom; with
   a Bronstedt base, wherein said Bronstedt base is a trivalent hydrocarbon compound of an element of column VB of the periodic table complexed with n molecules of hydrofluoric acid where n is at least 3 but not greater than 20.

31. The process of claim 30 wherein said Bronstedt base is $(CH_3CH_2)_3N \cdot 3HF$.

32. A process for the synthesis of a mixed halogen fluorocarbon compound comprising reacting:
   a hydrocarbon compound containing an $sp^3$-hybridized halophoric carbon atom bearing at least two halogen atom substituents, wherein at least two of the halogens have an atomic number greater than that of fluorine and said halophoric carbon atom is bonded to a sulfur atom; with
   a Bronstedt base, wherein said Bronstedt base is a trivalent hydrocarbon compound of an element of column VB of the periodic table complexed with n molecules of hydrofluoric acid where n is at least 3 but not greater than 20; and
   wherein said mixed halogen fluorocarbon compound has at least one more fluorine atom on the halophoric carbon atom than did the substrate hydrocarbon compound and has retained at least one halogen having an atomic number greater than that of fluorine on the halophoric carbon atom.

33. The process of claim 32, wherein n is not greater than 5.

34. The process of claim 33, wherein said Bronstedt base is $(CH_3CH_2)_3N \cdot 3HF$.

35. A process for the synthesis of a mixed halogen fluorocarbon compound comprising reacting:
   a hydrocarbon compound containing an $sp^3$-hybridized halophoric carbon atom bearing at least two halogen atom substituents, wherein at least two of the halogens have an atomic number greater than that of fluorine and said halophoric carbon atom is bonded to a chalcogen; with
   a Bronstedt base, wherein said Bronstedt base is a trivalent hydrocarbon compound of an element of column VB of the periodic table complexed with n molecules of hydrofluoric acid where n is at least 3 but not greater than 5; and
   wherein said mixed halogen fluorocarbon compound has at least one more fluorine atom on the halophoric carbon atom than did the hydrocarbon compound and has retained at least one halogen having an atomic number greater than that of fluorine on the halophoric carbon atom.

36. The process of claim 35, wherein said chalcogen is sulfur.

37. The process of claim 35, wherein said halogen having an atomic number greater than that of fluorine is chlorine.

38. The process of claim 35, wherein said Bronstedt base is $(CH_3CH_2)_3N \cdot 3HF$.

39. The process as defined by claim 1, wherein said Bronstedt base is a trivalent hydrocarbon pnictine compound.

40. The process of claim 17, wherein said Bronstedt base is a trivalent hydrocarbon pnictine compound.

41. The process of claim 30, wherein said Bronstedt base is a trivalent hydrocarbon pnictine compound.

42. The process of claim 32, wherein said Bronstedt base is a trivalent hydrocarbon pnictine compound.

43. The process of claim 35, wherein said Bronstedt base is a trivalent hydrocarbon pnictine compound.

* * * * *